US010696761B2

(12) United States Patent
Campbell et al.

(10) Patent No.: US 10,696,761 B2
(45) Date of Patent: *Jun. 30, 2020

(54) LIGHT GENERATING MICROCAPSULES FOR SELF-HEALING POLYMER APPLICATIONS

(71) Applicant: International Business Machines Corporation, Armonk, NY (US)

(72) Inventors: Eric J. Campbell, Rochester, MN (US); Sarah K. Czaplewski-Campbell, Rochester, MN (US); Joseph Kuczynski, North Port, FL (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/441,948

(22) Filed: Jun. 14, 2019

(65) Prior Publication Data
US 2019/0309105 A1  Oct. 10, 2019

Related U.S. Application Data

(63) Continuation of application No. 15/631,165, filed on Jun. 23, 2017, now Pat. No. 10,392,452.

(51) Int. Cl.
| | |
|---|---|
| *C09K 11/00* | (2006.01) |
| *C08J 5/00* | (2006.01) |
| *C01G 49/00* | (2006.01) |
| *C08F 20/06* | (2006.01) |
| *C08F 2/48* | (2006.01) |
| *B01J 13/14* | (2006.01) |
| *C07D 321/00* | (2006.01) |
| *C09B 6/00* | (2006.01) |
| *B01J 13/04* | (2006.01) |
| *B01J 13/22* | (2006.01) |
| *C08F 20/18* | (2006.01) |
| *A61K 9/50* | (2006.01) |

(52) U.S. Cl.
CPC .............. *C08F 20/06* (2013.01); *B01J 13/04* (2013.01); *B01J 13/14* (2013.01); *B01J 13/22* (2013.01); *C07D 321/00* (2013.01); *C08F 2/48* (2013.01); *C08F 20/18* (2013.01); *C09B 6/00* (2013.01); *A61K 9/5094* (2013.01)

(58) Field of Classification Search
None
See application file for complete search history.

(56) References Cited

U.S. PATENT DOCUMENTS

| | | |
|---|---|---|
| 3,481,790 A | 12/1969 | Duddy |
| 3,653,372 A | 4/1972 | Douglas |
| 3,656,372 A | 4/1972 | Chana |
| 3,689,391 A | 9/1972 | Ullman |
| 4,095,583 A | 6/1978 | Petersen |
| 4,233,402 A | 11/1980 | Maggio et al. |
| 4,273,671 A | 6/1981 | Allinikov |
| 4,278,837 A | 7/1981 | Best |
| 4,598,274 A | 7/1986 | Holmes |
| 4,635,166 A | 1/1987 | Cameron |
| 4,772,530 A | 9/1988 | Gottschalk |
| 4,811,288 A | 3/1989 | Kleijne |
| 4,814,949 A | 3/1989 | Elliott |
| 4,816,367 A | 3/1989 | Sakojiri |
| 5,169,707 A | 12/1992 | Faykish |
| 5,319,475 A | 6/1994 | Kay |
| 5,325,721 A | 7/1994 | Pendergrass, Jr. |
| 5,406,630 A | 4/1995 | Piosenka |
| 5,508,893 A | 4/1996 | Nowak |
| 5,904,795 A | 5/1999 | Murakami et al. |
| 5,904,796 A | 5/1999 | Freuler |
| 5,945,995 A | 8/1999 | Higuchi et al. |
| 5,984,995 A | 11/1999 | White |
| 6,114,413 A | 9/2000 | Kang |
| 6,217,213 B1 | 4/2001 | Curry |
| 6,235,148 B1 | 5/2001 | Courson, Jr. |
| 6,530,527 B1 | 3/2003 | Ahlers |
| 6,758,572 B2 | 7/2004 | Ladyjensky |

(Continued)

FOREIGN PATENT DOCUMENTS

| | | |
|---|---|---|
| CA | 918331 | 1/1973 |
| CN | 103740978 A | 4/2014 |

(Continued)

OTHER PUBLICATIONS

Xiong et al. "Towards Theranostic Multicompartment Microcapsules:in-situ Diagnostics and Laser-induced Treatment" Theranostics, vol. 3, Issue 3, 2013.*
Delcea et al. "Multicompartmental Micro and Nanocapsules: Hierarchy and Applications in Bioscience" 2010.*
Caruso et al. "Double-Walled Microcapsules for Self-healing Polymeric Materials" 2010.*
Brown et al., "In situ poly(urea-formaldehyde) microencapsulation of dicyclopentadiene," Taylor & Francis Health Sciences, Nov.-Dec. 2003, vol. 20, No. 6, 12 pages, DOI: 10.1080/02652040310001541 60.

(Continued)

*Primary Examiner* — Robert A Wax
*Assistant Examiner* — Danah Al-Awadi
(74) *Attorney, Agent, or Firm* — Robert J. Shatto

(57) ABSTRACT

A self-healing polymeric material includes a polymeric matrix material, wherein dispersed within the polymeric matrix material is a mixture of materials that includes monomers and a photoinitiator, and a plurality of light generating microcapsules dispersed in the polymeric matrix material. Each light generating microcapsule encapsulates multiple reactants that undergo a chemiluminescent reaction. The chemiluminescent reaction generates a photon having a wavelength within a particular emission range that is consistent with an absorption range of the photoinitiator.

20 Claims, 7 Drawing Sheets

(56) References Cited

U.S. PATENT DOCUMENTS

| | | | |
|---|---|---|---|
| 6,776,495 B2 | 8/2004 | Nomiyama | |
| 6,833,191 B2 | 12/2004 | Bayless | |
| 6,876,143 B2 | 4/2005 | Daniels | |
| 6,947,285 B2 | 9/2005 | Chen | |
| 7,005,733 B2 | 2/2006 | Kömmerling | |
| 7,065,656 B2 | 6/2006 | Schwenck | |
| 7,223,964 B2 | 5/2007 | Wiese | |
| 7,247,791 B2 | 7/2007 | Kulpa | |
| 7,248,359 B2 | 7/2007 | Boege | |
| 7,274,791 B2 | 9/2007 | van Enk | |
| 7,290,549 B2 | 11/2007 | Banerjee | |
| 7,296,299 B2 | 11/2007 | Schwenck | |
| 7,362,248 B2 | 4/2008 | McClure | |
| 7,385,491 B2 | 6/2008 | Doi | |
| 7,436,316 B2 | 10/2008 | Fleischman | |
| 7,443,176 B2 | 10/2008 | McClure | |
| 7,488,954 B2 | 2/2009 | Ross | |
| 7,518,507 B2 | 4/2009 | Dalzell | |
| 7,540,621 B2 | 6/2009 | Goychrach | |
| 7,573,301 B2 | 8/2009 | Walmsley | |
| 7,666,813 B2 | 2/2010 | Hoefer et al. | |
| 7,806,072 B2 | 10/2010 | Hamilton, II | |
| 7,816,785 B2 | 10/2010 | Iruvanti | |
| 7,830,021 B1 | 11/2010 | Wilcoxon | |
| 7,834,442 B2 | 11/2010 | Furman | |
| 7,886,813 B2 | 2/2011 | Hua | |
| 7,889,442 B2 | 2/2011 | Suzuki et al. | |
| 7,952,478 B2 | 5/2011 | Bartley | |
| 8,137,597 B1 * | 3/2012 | Brott | F21K 2/06 252/700 |
| 8,174,112 B1 | 5/2012 | Karp | |
| 8,198,641 B2 | 6/2012 | Zachariasse | |
| 8,288,857 B2 | 10/2012 | Das | |
| 8,310,147 B2 | 11/2012 | Seo | |
| 8,502,396 B2 | 8/2013 | Buer | |
| 8,522,049 B1 | 8/2013 | Ahmadi | |
| 8,581,209 B2 | 11/2013 | Oxley | |
| 8,623,418 B2 | 1/2014 | Liang | |
| 8,647,579 B2 | 2/2014 | La Grone | |
| 8,659,908 B2 | 2/2014 | Adams | |
| 8,741,084 B2 | 6/2014 | Kisch et al. | |
| 8,741,804 B2 | 6/2014 | Boday | |
| 8,824,040 B1 | 9/2014 | Buchheit | |
| 8,865,285 B2 | 10/2014 | Dagher | |
| 8,896,100 B2 | 11/2014 | Kishino et al. | |
| 8,896,110 B2 | 11/2014 | Hu | |
| 9,040,252 B2 | 5/2015 | Della Ciana | |
| 9,075,018 B2 | 7/2015 | Geddes | |
| 9,217,736 B2 | 12/2015 | Ribi | |
| 9,245,202 B2 | 1/2016 | Boday | |
| 9,263,605 B1 | 2/2016 | Morgan | |
| 9,307,692 B2 | 4/2016 | Boday | |
| 9,856,404 B2 | 1/2018 | Campbell | |
| 9,858,780 B1 | 1/2018 | Campbell | |
| 9,896,389 B2 | 2/2018 | Campbell | |
| 10,040,993 B1 * | 8/2018 | Brott | F21K 2/06 |
| 10,229,292 B2 | 3/2019 | Campbell | |
| 10,318,462 B2 | 6/2019 | Bartley | |
| 10,331,911 B2 | 6/2019 | Kuczynski | |
| 10,357,921 B2 | 7/2019 | Campbell | |
| 10,392,452 B2 | 8/2019 | Campbell et al. | |
| 10,508,204 B2 | 12/2019 | Odarczenko | |
| 2005/0068760 A1 | 3/2005 | Goychrach | |
| 2006/0079021 A1 | 4/2006 | Yang | |
| 2006/0228542 A1 | 10/2006 | Czubarow | |
| 2007/0054762 A1 | 3/2007 | Tocco | |
| 2007/0207284 A1 | 9/2007 | McClintic | |
| 2008/0038540 A1 | 2/2008 | Hirayama | |
| 2008/0090942 A1 | 4/2008 | Hovorka | |
| 2008/0277596 A1 | 11/2008 | Oxley | |
| 2008/0286856 A1 | 11/2008 | Park | |
| 2009/0036568 A1 | 2/2009 | Merle | |
| 2009/0155571 A1 | 6/2009 | Mustonen | |
| 2010/0006431 A1 | 1/2010 | Wallace | |
| 2012/0007249 A1 | 1/2012 | Kuo et al. | |
| 2012/0077279 A1 | 3/2012 | Wiesner | |
| 2013/0034739 A1 | 2/2013 | Boday | |
| 2013/0179996 A1 | 7/2013 | Boday | |
| 2014/0011049 A1 | 1/2014 | Stamm | |
| 2014/0110049 A1 | 4/2014 | Yuen | |
| 2014/0110469 A1 | 4/2014 | Wang et al. | |
| 2014/0368992 A1 | 12/2014 | Strader | |
| 2015/0038809 A1 | 2/2015 | Etzkorn | |
| 2015/0166822 A1 | 6/2015 | Samsudin | |
| 2015/0246521 A1 | 9/2015 | Fathi | |
| 2015/0364710 A1 | 12/2015 | Chen | |
| 2016/0033497 A1 | 2/2016 | Wang | |
| 2016/0053169 A1 | 2/2016 | Kunath | |
| 2016/0067524 A1 | 3/2016 | Bourke, Jr. | |
| 2016/0289484 A1 | 10/2016 | Lalgudi | |
| 2017/0015886 A1 | 1/2017 | Braun et al. | |
| 2017/0027197 A1 | 2/2017 | Bourke, Jr. | |
| 2017/0029532 A1 | 2/2017 | Pandya | |
| 2017/0129825 A1 | 5/2017 | Campbell | |
| 2017/0130102 A1 | 5/2017 | Campbell | |
| 2017/0130993 A1 | 5/2017 | Campbell | |
| 2017/0158886 A1 * | 6/2017 | Odarczenko | C09D 163/00 |
| 2017/0279532 A1 | 9/2017 | Bartley | |
| 2018/0116060 A1 | 4/2018 | Campbell | |
| 2018/0327659 A1 | 11/2018 | Campbell | |
| 2018/0340032 A1 | 11/2018 | Campbell et al. | |
| 2018/0340850 A1 | 11/2018 | Campbell | |
| 2018/0371122 A1 | 12/2018 | Campbell et al. | |
| 2018/0371123 A1 | 12/2018 | Campbell | |
| 2019/0291357 A1 | 9/2019 | Campbell et al. | |

FOREIGN PATENT DOCUMENTS

| | | | |
|---|---|---|---|
| CN | 103740997 A | | 4/2014 |
| JP | 2000317578 A | | 11/2000 |
| JP | 2001176924 A | | 6/2001 |
| JP | 4073571 B2 | | 2/2008 |
| WO | 9733922 A1 | | 9/1997 |
| WO | WO 97/33922 | * | 9/1997 |
| WO | 2009029804 A2 | | 3/2009 |
| WO | 2011086018 A1 | | 7/2011 |
| WO | 2013041871 A2 | | 3/2013 |
| WO | 2014204823 A1 | | 12/2014 |
| WO | 2014204828 A2 | | 12/2014 |
| WO | 2016186336 A1 | | 11/2016 |

OTHER PUBLICATIONS

Caruso et al. "Robust, Double-Walled Microcapsules for Self-Healing Polymeric Materials," ACS Applied Materials & Interfaces, 2010, vol. 2, No. 4, pp. 1195-1199.

Delcea et al., "Multicompartmental Micro- and Nanocapsules: Hierarchy and Applications in Biosciences", Macromolecular Bioscience, vol. 10, 2010, pp. 465-474.

Hu et al., Controlled Rupture of Magnetic Polyelectrolyte Microcapsules for Drug Delivery, Langmuir, vol. 24, Sep. 2008, pp. 11811-11818, American Chemical Society, USA.

Jorgensen et al., A Biochemical Microdevice With an Integrated Chemiluminescence Detector, Sensors and Actuators B: Chemical, vol. 90, Issue 1, Apr. 2003, pp. 15-21, Elsevier, Amsterdam, Netherlands.

Kawashita et al., In vitro heat generation by ferrimagnetic maghemite microspheres for hyperthermic treatment of cancer under alternating magnetic field, Journal of Materials Science: Materials in Medicine, vol. 19, Issue 5, pp. 1897-1903, May 2008, (Abstract Only, 2 pages), URL: www.ncbi.nlm.nih.gov/pubmed/17914614.

Keller et al., Mechanical Properties of Microcapsules Used in a Self-Healing Polymer, Experimental Mechanics, vol. 16, Nov. 2006, pp. 725-733, Society for Experimental Mechanics, Bethel, CT.

Kreft et al., "Shell-in-Shell Microcapsules: A Novel Tool for Integrated, Spatially Confined Enzymatic Reactions", Angewandte Chemie, Int. Ed., Jul. 2007 (online Jun. 2007), vol. 46, Issue 29, pp. 5605-5608, Wiley-VCH Verlag GmbH & Co., KGaA, Weinheim, DOI: 10.1002/anie.200701173.

Lee, Microencapsulated Heat Generating Material to Accelerate the Curing Process During Liquid Crystal Display Fabrication, NineSigma,

(56) References Cited

OTHER PUBLICATIONS

Inc. (online), 2014 (month unknown), 3 pages, accessed Jun. 5, 2017, URL: https://ninesights.ninesigma.com/rfps/-/rfp-portlet/rfpViewer/2690.
List of IBM Patents or Patent Applications Treated as Related, Jun. 14, 2019, 2 pages.
Marzzacco, C., "The Effect of a Change in the Catalyst on the Enthalpy of Decomposition of Hydrogen Peroxide," pp. 12-13, Chem 13 News/Nov. 2008, reprinted from pp. 16-17, May 2001.
Masin, The Chemistry of Hand Warmers, 3 pages, chemistryislife.com (online), accessed Jun. 5, 2017, URL: www.chemistryislife.com/the-chemistry- of-hand-warmer.
Parakhonskiy, "Colloidal micro- and nano-particles as templates for polyelectrolyte multilayer capsules", Advances in Colloid and Interface Science, May 2014, vol. 207, pp. 253-264, ScienceDirect.com (online), Elsevier B.V., Amsterdam.
Park et al., Smart Microplates: Integrated Photodiodes for Detecting Bead-Based Chemiluminescent Reactions, 5th IEEE Conference on Sensors, EXCO, (IEEE Sensors 2006), held Oct. 2006, Daegu, Korea, pp. 580-583, Institute of Electrical and Electronics Engineers (IEEE), DOI: 10.1109/ICSENS.2007.355534, USA.
Previte et al., Microwave-Triggered Metal-Enhanced Chemiluminescence (MT-MEC): Application to Ultra-Fast and Ultra-Sensitive Clinical Assays, Journal of Fluorescence, vol. 16, Issue 5, Sep. 2006, pp. 641-647, Springer Science+Business Media, Berlin, Germany.
Stober et al., Controlled Growth of Monodisperse Silica Spheres in the Micron Size Range, Journal of Colloid and Interface Science, vol. 26, Jan. 1968, pp. 62-69, Elsevier Inc., Amsterdam.
U.S. Appl. No. 16/441,853, to Eric J. Campbell et al., entitled, "Light Generating Microcapsules for Photo-Curing", assigned to International Business Machines Corporation, 27 pages, filed Jun. 14, 2019.
Unknown, "Flameless Chemical Heaters", 2014, zenstoves.net, 4 pages, printed from <http://zenstoves.net/Flameless.htm> on Sep. 14, 2015.
Unknown, Advanced Technologies for LCD Assembly, DowCorning.com (online), 2014 (month unknown), 4 pages, accessed Jun. 5, 2017, URL: www.dowcoming.com/content/publishedlit/11-3437_Advanced_Technologies_LCD_Assembly.pdf?wt.svl=ELEC_LHH.
Unknown, Flameless Ration Heater (FRH), MREInfo.com (online), 2014, 5 pages, accessed Jun. 5, 2017, URL: www.mreinfo.com/us/mre/frh.html.
Unknown, Loctite Eccobond DS 6601, Henkel.com (online), Mar. 2013, 2 pages, URL: https://tds.us.henkel.com/NA/UT/HNAUTTDS.nsf/web/C0DD8377AB27D63985257B41005DC4A1/$File/LOCTITE%20ECCOBOND%20DS%206601-EN.pdf.
Unknown, Materials for Sealing Liquid Crystal, Three Bond Technical News, vol. 43, May 1994, pp. 1-8, Three Bond Europe, UK.
Unknown, PTFE Coatings, Specific Heat of Some Common Substances, engineeringtoolbox.com (online), 7 pages, accessed Jun. 5, 2017, URL: www.engineeringtoolbox.com/specific-heat-capacity-d_391.html.
Unknown, Standard enthalpy change of formation (data table), Wikipedia.org (online), 13 pages, accessed Jun. 5, 2017, URL: en.wikipedia.org/wiki/Standard_enthalpy_change_of_formation_%28data_table%29.
Unknown, Technical Overview: Microencapsulation, microteklabs.com (online), 4 pages, accessed Jun. 5, 2017, URL: www.microteklabs.com/technical_overview.pdf.
Unknown, Thermochemistry, 7 pages, Olomouc—Hejĉín Gymnasium (online), 7 pages, accessed Jun. 5, 2017, URL: http://smd.gytool.cz/downloads/thermochemistry_bar.pdf.
Xiong et al., "Towards Theranostic Multicompartment Microcapsules: in-situ Diagnostics and Laser-induced Treatment", Theranostics, vol. 3, Issue 3, Feb. 2013, pp. 141-151, Ivyspring International, Sydney, Australia.
Yamaura et al., "Preparation and characterization of (3-aminopropyl) triethoxysilane-coated magnetite nanoparticles", Journal of Magnetism and Magnetic Materials, vol. 279, Issues 2-3, Aug. 2004, pp. 210-217, ScienceDirect.com (online), Elsevier B.V., Amsterdam.
Zhan et al., Electrochemical Sensing in Microfluidic Systems Using Electrogenerated Chemiluminescence As A Photonic Reporter of Redox Reactions, JACS Articles, vol. 124, No. 44, Oct. 2002, pp. 13265-13270, American Chemical Society, Washington, D.C.
Engineering ToolBox, (2003). Specific Heat of some common Substances. [online] Available at: https://www.engineeringtoolbox.com/specific-heat-capacity-d_391.html [Accessed Jan. 9, 2020].
List of IBM Patents or Patent Applications Treated as Related, Jan. 16, 2020, 2 pages.

\* cited by examiner

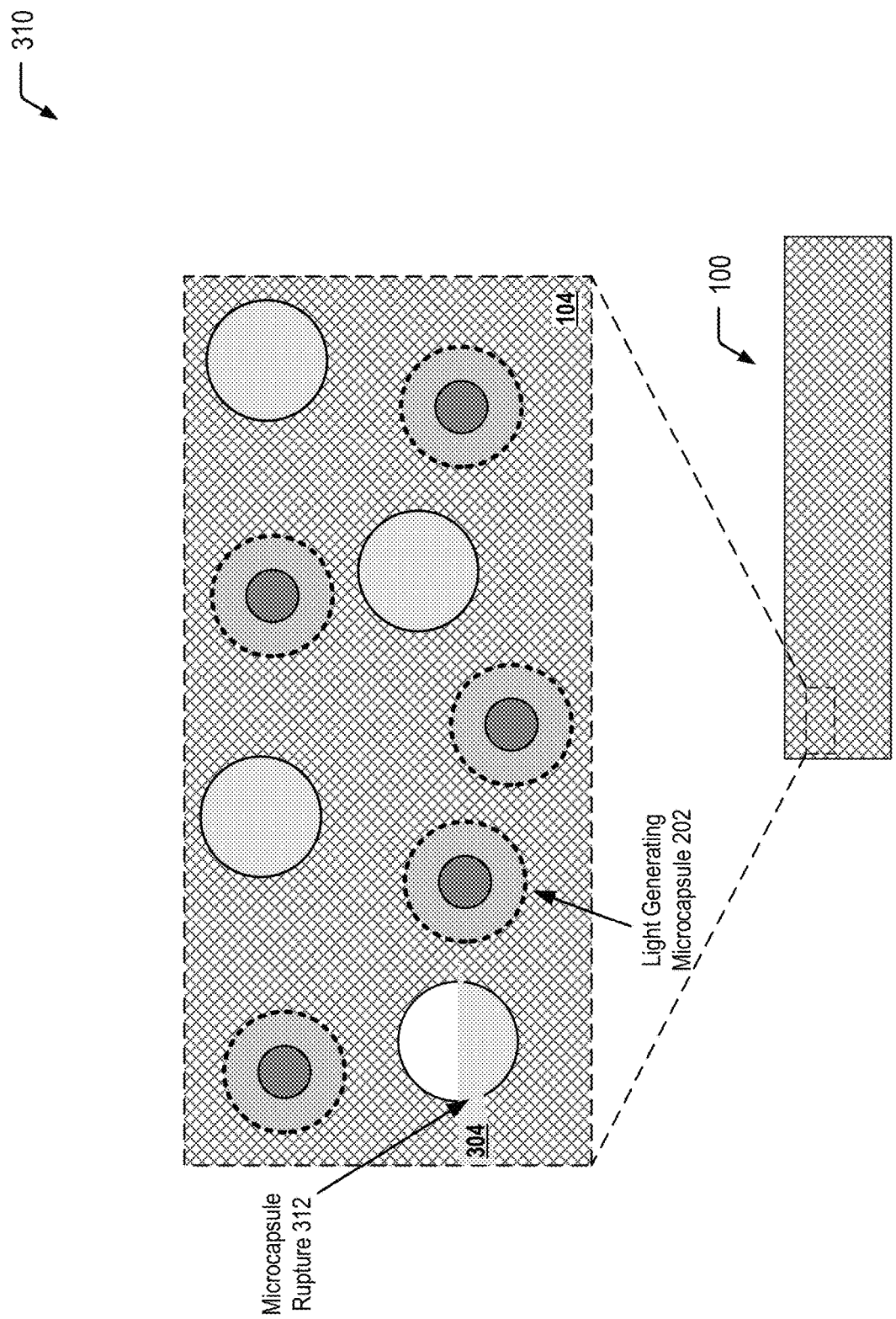

LIGHT GENERATING MICROCAPSULES FOR SELF-HEALING POLYMER APPLICATIONS

BACKGROUND

Typical self-healing polymers utilize encapsulated monomers that react in the presence of a catalyst that is incorporated into the polymer matrix. The healing material is limited in selection because a proper monomer/catalyst pair must be compatible with the polymer matrix. Additionally, self-healing schemes typically involve thermally initiated reactions. In some cases (e.g., outdoor applications with low ambient temperatures), such thermally initiated reactions may proceed too slowly to repair damage at an early stage.

SUMMARY

According to an embodiment, a self-healing polymeric material is disclosed that includes a polymeric matrix material, wherein dispersed within the polymeric matrix material is a mixture of materials that includes monomers and a photoinitiator, and a plurality of light generating microcapsules dispersed in the polymeric matrix material. Each light generating microcapsule encapsulates multiple reactants that undergo a chemiluminescent reaction. The chemiluminescent reaction generates a photon having a wavelength within a particular emission range that is consistent with an absorption range of the photoinitiator.

According to another embodiment, a process of utilizing chemiluminescence for polymeric self-healing is disclosed. The process includes dispersing a monomer mixture in a polymeric matrix material. The monomer mixture is a mixture of materials that includes monomers and a photoinitiator. The process also includes dispersing a light generating microcapsule in the polymeric matrix material. The light generating microcapsule encapsulates multiple reactants that undergo a chemiluminescent reaction. The chemiluminescent reaction generates a photon having a wavelength within a particular emission range that is consistent with an absorption range of the photoinitiator. The light generating microcapsule is adapted to cause the multiple reactants to undergo the chemiluminescent reaction within the light generating microcapsule in response to application of a compressive force.

According to another embodiment, an in-situ light generation process is disclosed that includes forming an article of manufacture that includes a self-healing polymeric material. The self-healing polymeric material includes a polymeric matrix material, wherein dispersed within the polymeric matrix material is a mixture of materials that includes monomers and a photoinitiator, and a plurality of light generating microcapsules dispersed in the polymeric matrix material. Each light generating microcapsule encapsulates multiple reactants that undergo a chemiluminescent reaction. The chemiluminescent reaction generates a photon having a wavelength within a particular emission range that is consistent with an absorption range of the photoinitiator. The process also includes exposing the article of manufacture to an environment that results in formation of a crack in the polymeric matrix material. The crack causes migration of the mixture of materials into the crack. The chemiluminescent reaction within the light generating microcapsule generates sufficient light to cause the photoinitiator to initiate a polymerization reaction of the monomers within the crack. The polymerization reaction results in formation of a polymeric material that seals the crack.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIG. 3B is a cross-sectional view of selected portions of the article of manufacture of FIG. 1 at a second stage of propagation of the crack resulting in rupture of a monomer mixture microcapsule and release of a monomer mixture (that includes monomers and a photoinitiator) to fill the crack, according to one embodiment.

DETAILED DESCRIPTION

The present disclosure describes light generating microcapsules and processes of utilizing the light generating microcapsules for in-situ generation of light for self-healing polymeric applications. Chemiluminescence is the emission of photons as the result of a chemical reaction. In the present disclosure, a light generating microcapsule includes multiple compartments to isolate a first reactant (or a first set of reactants) from a second reactant (or a second set of reactants) within the same microcapsule. Application of a particular stimulus (e.g., a compressive force) to the multiple-compartment microcapsule results in rupture of an inner compartment, enabling the first reactant(s) and the second reactant(s) to mix and undergo a chemiluminescent reaction within the microcapsule.

The light generating microcapsules of the present disclosure may be dispersed within a polymeric matrix material (also referred to herein as a "self-healing polymeric matrix material") to enable photons to be generated in situ within the polymeric matrix material. In some embodiments of the present disclosure, the polymeric matrix material further includes a second set of microcapsules (also referred to herein as "monomer mixture microcapsules") that encapsulate a mixture of materials that includes monomers and a photoinitiator. The photoinitiator may create reactive species (e.g., free radicals, cations, or anions) when exposed to radiation (e.g., UV or visible light). In a particular embodiment, the photoinitiator may correspond to a free radical initiator to initiate a free-radical polymerization reaction. In alternative embodiments, rather than utilizing microcapsules to encapsulate the mixture, the monomers and the photoinitiator may be dispersed throughout the polymeric matrix material.

Figure 3A:
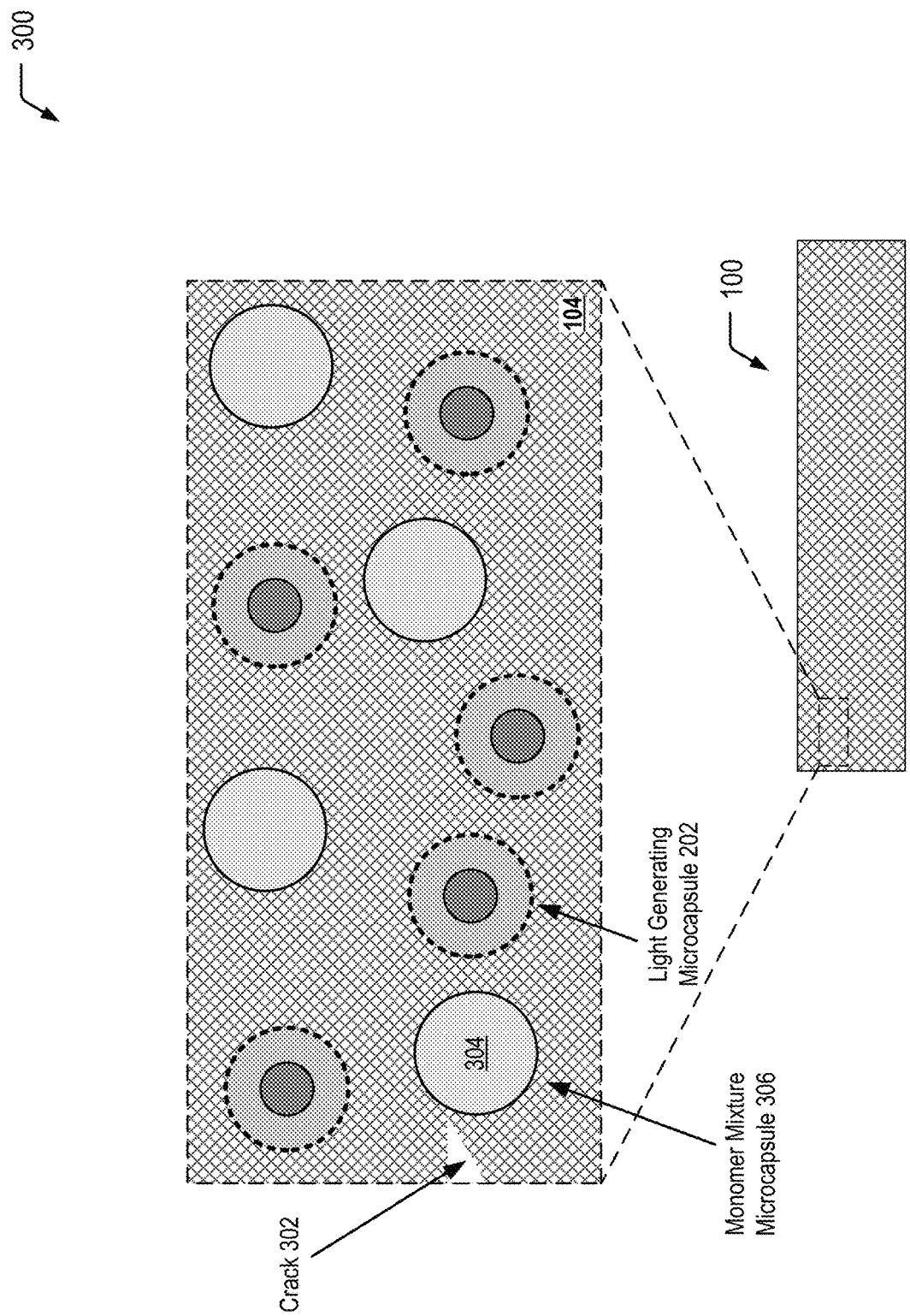
FIG. 3A is a cross-sectional view of selected portions of the article of manufacture of FIG. 1 at a first stage of propagation of a crack in the self-healing polymeric matrix material, according to one embodiment.
Figure 3C:
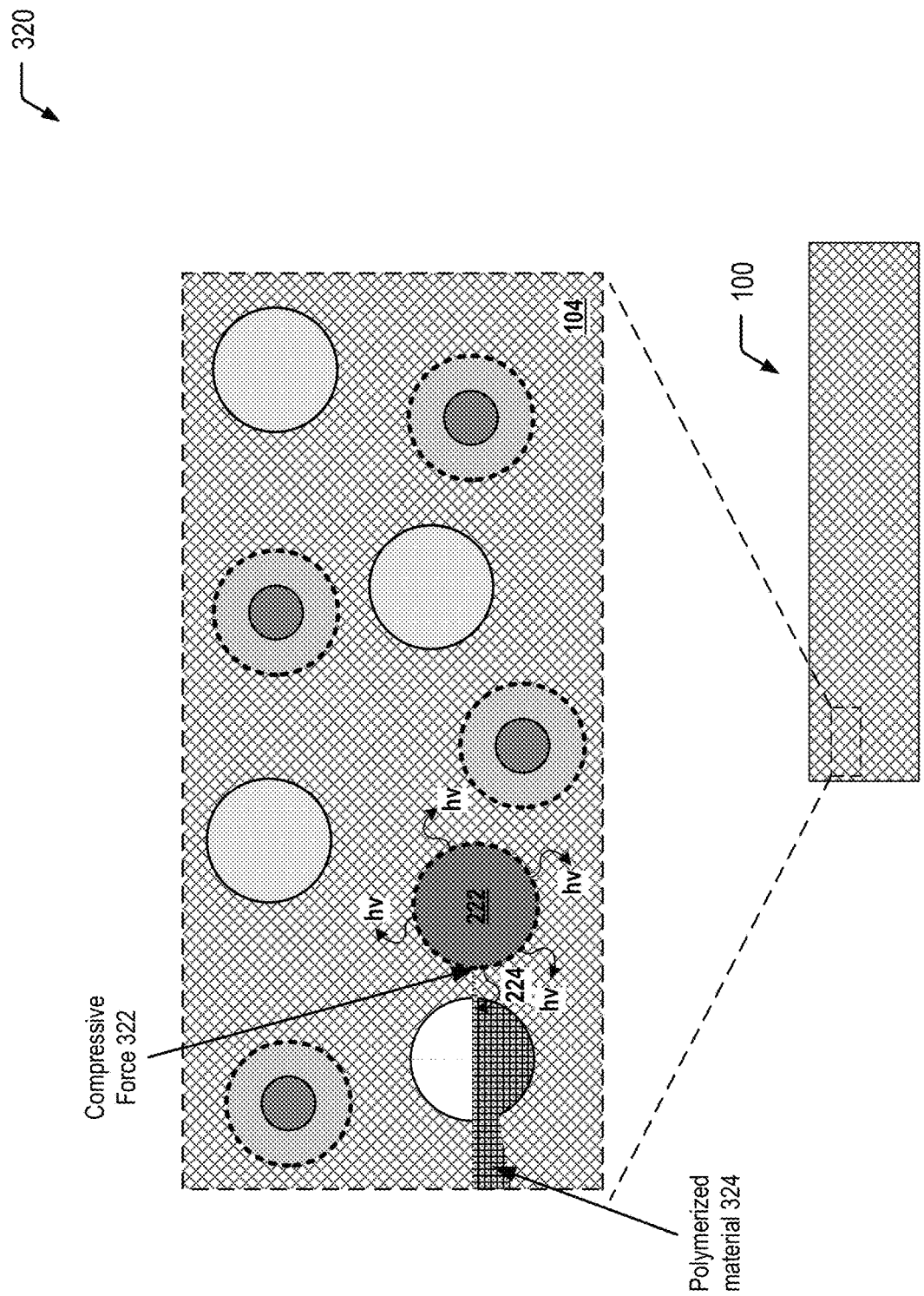
FIG. 3C is a cross-sectional view of selected portions of the article of manufacture of FIG. 1 at a third stage of propagation of the crack causing a compressive force to a light generating microcapsule resulting in a chemiluminescent reaction with a photon emission wavelength that is satisfactory to excite the photoinitiator in order to initiate polymerization of the monomers to seal the crack, according to one embodiment.

As illustrated and described further herein with respect to FIGS. 3A-3C, propagation of a crack in the self-healing polymeric matrix material results in rupture of a monomer mixture microcapsule (or multiple microcapsules), causing the monomers and the photoinitiator to fill the crack. Further propagation of the crack results in application of a compressive force to a light generating microcapsule (or multiple microcapsules), triggering the chemiluminescent reaction within the light generating microcapsule. An outer shell of the light generating microcapsule may be formed from a material that enables a substantial portion of the photons generated within the microcapsule to exit into the surrounding material(s), including the monomer mixture that has filled the crack. The emitted light is within a particular wavelength range that is satisfactory to excite the photoinitiator to create reactive species (e.g., free radicals) to trigger polymerization (e.g., free radical polymerization) of the monomers that have filled the crack. Thus, in contrast to existing polymeric self-healing schemes that involve a thermally initiated reaction, the light-triggered self-healing mechanism of the present disclosure enables polymeric self-healing without employing other means, such as an external heat source to accelerate a thermally initiated reaction.

As used herein, the term "light" is used to refer to ultraviolet (UV) light (in a wavelength range of 10 nm to 400 nm), visible light (e.g., in a wavelength range of 400 nm to 700 nm), or infrared light (e.g., above 700 nm) that may be produced as a result of a chemiluminescent reaction. As used herein, the term "microcapsule" is used to refer to capsules that are in a range of about 10 microns to 1000 microns in diameter. However, it will be appreciated that the following disclosure may be applied to capsules having a smaller size (also referred to as "nanocapsules").

Figure 1:
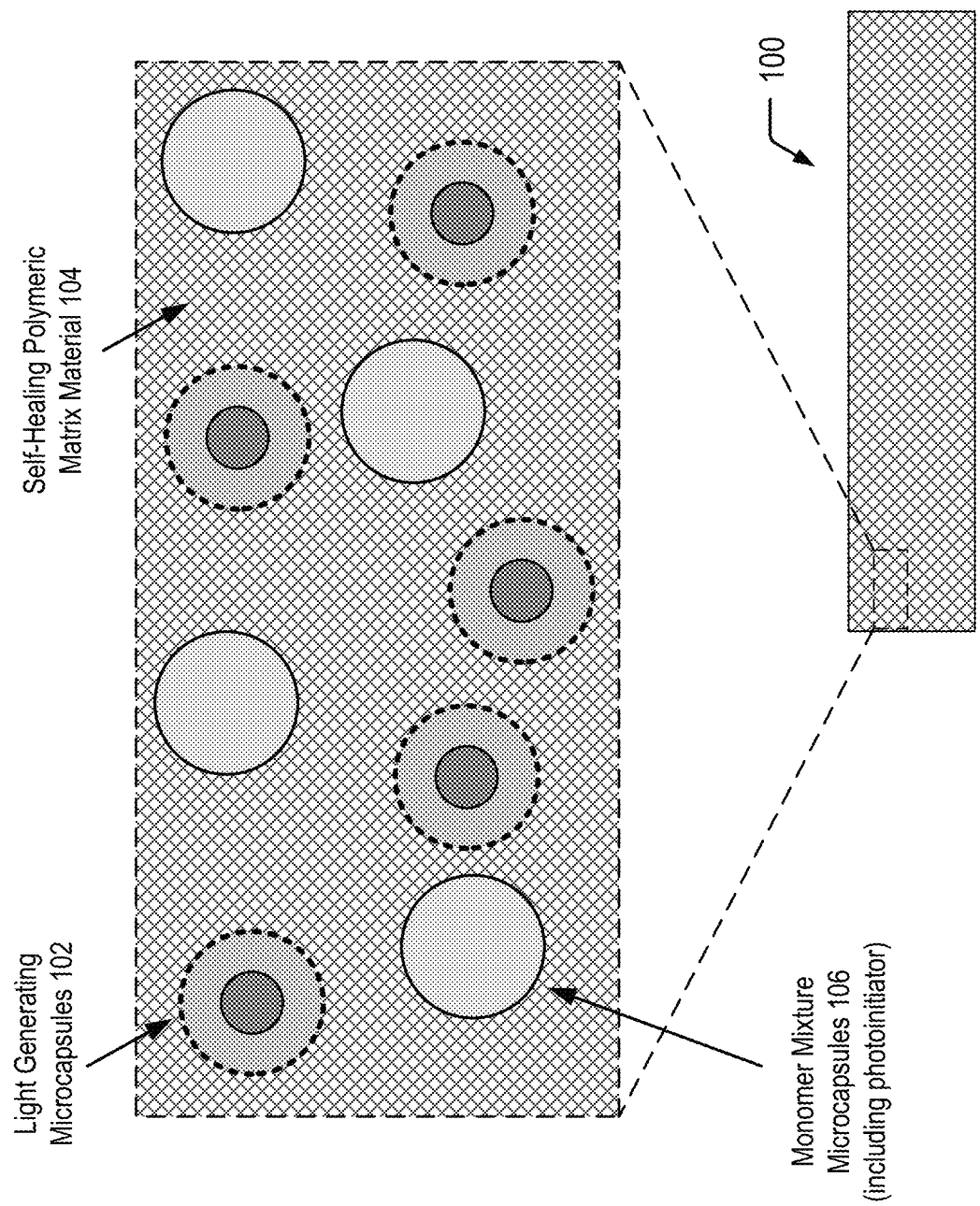
FIG. 1 is a cross-sectional view of selected portions of an article of manufacture that utilizes light generating microcapsules for polymeric self-healing, according to one embodiment.

FIG. 1 illustrates a cross-sectional view of selected portions of an article of manufacture 100 that utilizes light generating microcapsules 102 for polymeric self-healing, according to one embodiment. In FIG. 1, a self-healing polymeric matrix material 104 includes a plurality of the light generating microcapsules 102 and a plurality of monomer mixture microcapsules 106 dispersed therein. The monomer mixture microcapsules 106 may encapsulate a mixture of monomers (e.g., acrylate monomers) and a photoinitiator (e.g., a free radical initiator). As illustrated and further described herein with respect to FIGS. 3A-3C, propagation of a crack in the self-healing polymeric matrix material 104 may result in rupture of at least one of the monomer mixture microcapsules 106, causing the encapsulated mixture (including the photoinitiator) to fill the crack. Further propagation of the crack results in application of a compressive force to at least one of the light generating microcapsules 102, triggering a chemiluminescent reaction within at least one of the light generating microcapsules 102. The emitted photons are within a particular wavelength range that is satisfactory to cause the photoinitiator to generate free radicals to initiate polymerization of the monomers to "heal" the self-healing polymeric matrix material 104 by forming a polymerized material that seals the crack.

In FIG. 1, the monomer mixture microcapsules 106 are shown prior to the formation of a crack in the self-healing polymeric matrix material 104 that results in rupture of at least one of the monomer mixture microcapsules 106, causing the encapsulated mixture to fill the crack. As illustrated and further described herein with respect to FIGS. 3A and 3B, a crack in the self-healing polymeric matrix material 104 may result in the rupture of one (or more) of the monomer mixture microcapsules 106 and the release of the encapsulated monomer mixture into the crack. As illustrated and further described herein with respect to FIG. 3C, the photons generated within one (or more) of the light generating microcapsules 102 may excite the photoinitiator (e.g., a free radical initiator) to initiate a polymerization reaction (e.g., a free radical polymerization reaction) to form a cross-linked material that seals the crack, thereby preventing further propagation of the crack.

The monomers encapsulated within the monomer mixture microcapsules 106 may correspond to an acrylate monomer, an epoxide monomer, or another type of monomer that undergoes a particular type of polymerization reaction triggered by the photoinitiator (e.g., a free radical polymerization reaction in the case of a free radical initiator). The monomers begin to polymerize as the photoinitiator is energized by radiation from a chemiluminescent light source.

The light generating microcapsules 102 illustrated in FIG. 1 include multiple compartments and are also referred to herein as multiple-compartment microcapsules. In FIG. 1, the light generating microcapsules 102 are shown prior to application of a compressive force that results in a chemiluminescent reaction within the individual light generating microcapsules 102. Accordingly, FIG. 1 illustrates that the compartments of the light generating microcapsules 102 enable isolation of reactants in order to prevent the chemiluminescent reaction prior to application of the compressive force.

In the particular embodiment depicted in FIG. 1, the light generating microcapsules 102 dispersed in the self-healing polymeric matrix material 104 have a shell-in-shell architecture with an inner shell contained within an outer shell, where the inner shell is adapted to rupture in response to application of a compressive force in order to trigger a chemiluminescent reaction within the light generating microcapsules 102. Thus, the individual light generating microcapsules 102 depicted in FIG. 1 may correspond to the multiple-compartment microcapsule (having a shell-in-shell architecture) formed according to the process described herein with respect to FIG. 4. It will be appreciated that, in alternative embodiments, the light generating microcapsules 102 may have an alternative multiple-compartment microcapsule design, may include more than one type of multiple-compartment microcapsule design, or a combination thereof.

As described further herein, the chemiluminescent reaction generates actinic photons within a particular wavelength range that is satisfactory to excite a particular photoinitiator to initiate polymerization of the monomers. The outer shell of the light generating microcapsules 102 allows a substantial portion of the actinic photons generated within the microcapsules 102 as a result of the chemiluminescent reaction to pass through the outer shell into the surrounding material(s). As described further herein with respect to FIG. 4, the outer shell can be made from chemically non-reactive materials, such as some plastics which are transparent, translucent, or light filtering to pass the appropriate wavelengths of light into the surrounding material(s). In a particular embodiment, the outer shell has a transmittance value of at least 90% for the particular emitted photon wavelength(s). In certain embodiments, the outer shell may include a natural polymeric material, such as gelatin, arabic gum, shellac, lac, starch, dextrin, wax, rosin, sodium alginate, zein, and the like; semi-synthetic polymer material, such as methyl cellulose, ethyl cellulose, carboxymethyl cellulose, hydroxyethyl ethyl cellulose; full-synthetic polymer material, such as polyolefins, polystyrenes, polyethers, polyureas, polyethylene glycol, polyamide, polyurethane, polyacrylate, epoxy resins, among others.

Thus, FIG. 1 illustrates an example of an article of manufacture that includes light generating microcapsules dispersed in a polymeric matrix material to enable self-healing of the polymeric matrix material. As illustrated and further described herein with respect to FIGS. 3A-3C, propagation of a crack in the polymeric matrix material causes the monomer mixture microcapsule(s) dispersed in the polymeric matrix material to rupture and release the encapsulated monomer mixture (including the photoinitiator) into the crack. Further propagation of the crack results in application of a compressive force to the light generating microcapsule(s) that triggers a chemiluminescent reaction within the light generating microcapsule(s). The chemiluminescent reaction emits light of sufficient energy to excite the photoinitiator for polymerization of the monomers that have filled the crack, thereby "healing" the polymeric matrix material by forming a polymerized material that seals the crack to prevent further propagation of the crack.

Figure 2A:
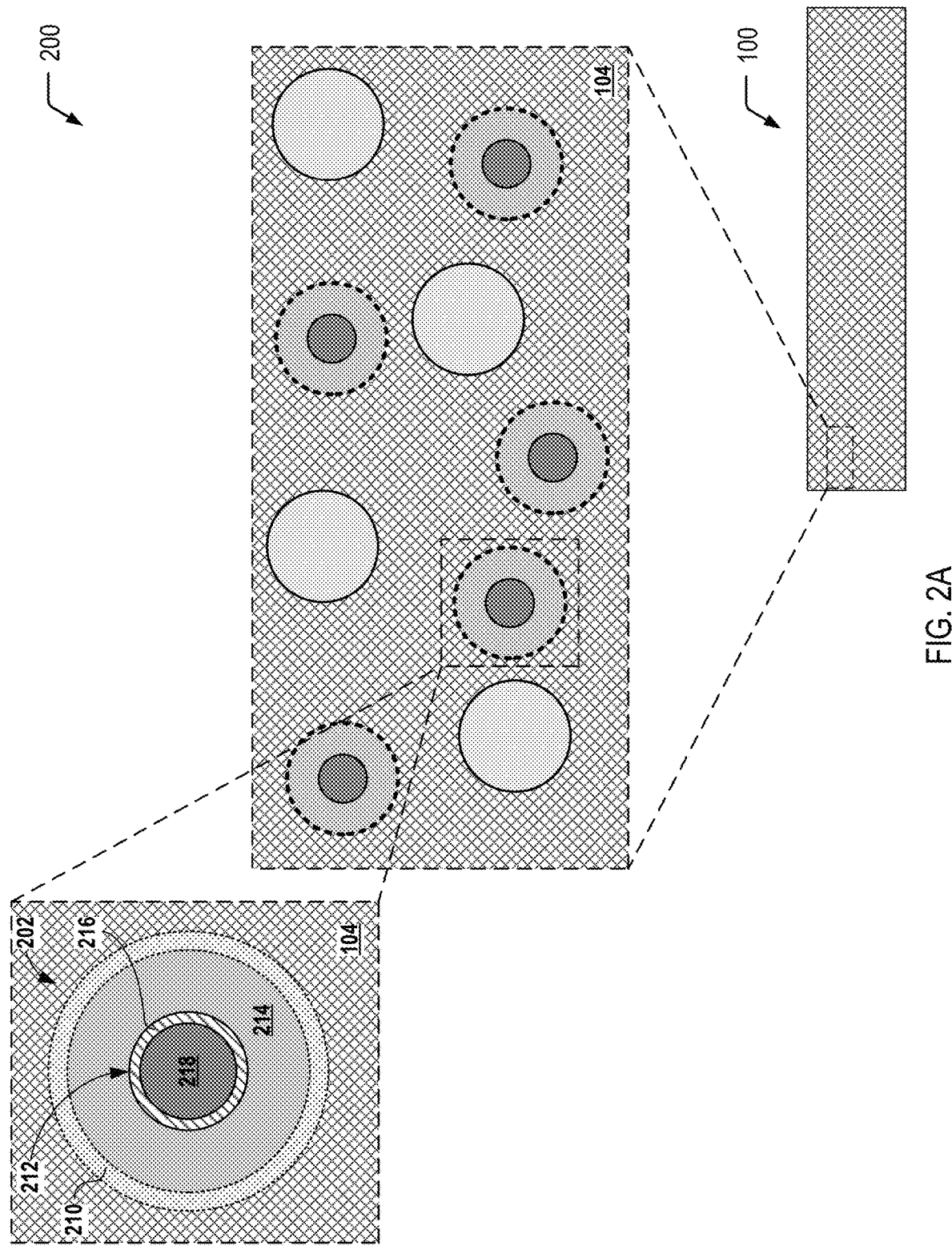
FIG. 2A is a cross-sectional view of a multiple-compartment microcapsule corresponding to one of the light generating microcapsules depicted in FIG. 1, in which reactants that undergo a chemiluminescent reaction are isolated within individual compartments of the microcapsule, according to one embodiment.

FIG. 2A illustrates an exploded cross-sectional view 200 of a multiple-compartment microcapsule 202 corresponding to one of the plurality of the light generating microcapsules 102 depicted in FIG. 1, according to one embodiment. In FIG. 2A, the multiple-compartment microcapsule 202 is shown prior to application of a compressive force to the multiple-compartment microcapsule 202. In FIG. 2A, reactants that undergo a chemiluminescent reaction are isolated within individual compartments of the multiple-compartment microcapsule 202. As illustrated and further described herein with respect to FIG. 2B, application of a compressive force to the multiple-compartment microcapsule 202 depicted in FIG. 2A (e.g., as a result of a crack in the self-healing polymeric matrix material 104) enables the isolated reactants to mix and undergo the chemiluminescent reaction within the multiple-compartment microcapsule 202.

The exploded cross-sectional view 200 of FIG. 2A illustrates a particular embodiment in which the multiple-compartment microcapsule 202 has an outer wall 210 (also referred to herein as the "outer shell") and contains an inner microcapsule 212 and a first reactant 214 (or a first set of multiple reactants). The inner microcapsule 212 has a capsule wall 216 (also referred to herein as the "inner shell") and contains a second reactant 218 (or a second set of multiple reactants). The first reactant(s) 214 within the microcapsule 202 may surround the inner microcapsule 212, and the first reactant(s) 214 may be prevented from contacting the second reactant(s) 218 by the capsule wall 216 of the inner microcapsule 212. In a particular embodiment, the capsule wall 216 of the inner microcapsule 212 may be formed to rupture under a particular compressive force, and the outer wall 210 of the microcapsule 202 may be formed so as to not rupture under that compressive force.

Figure 2B:
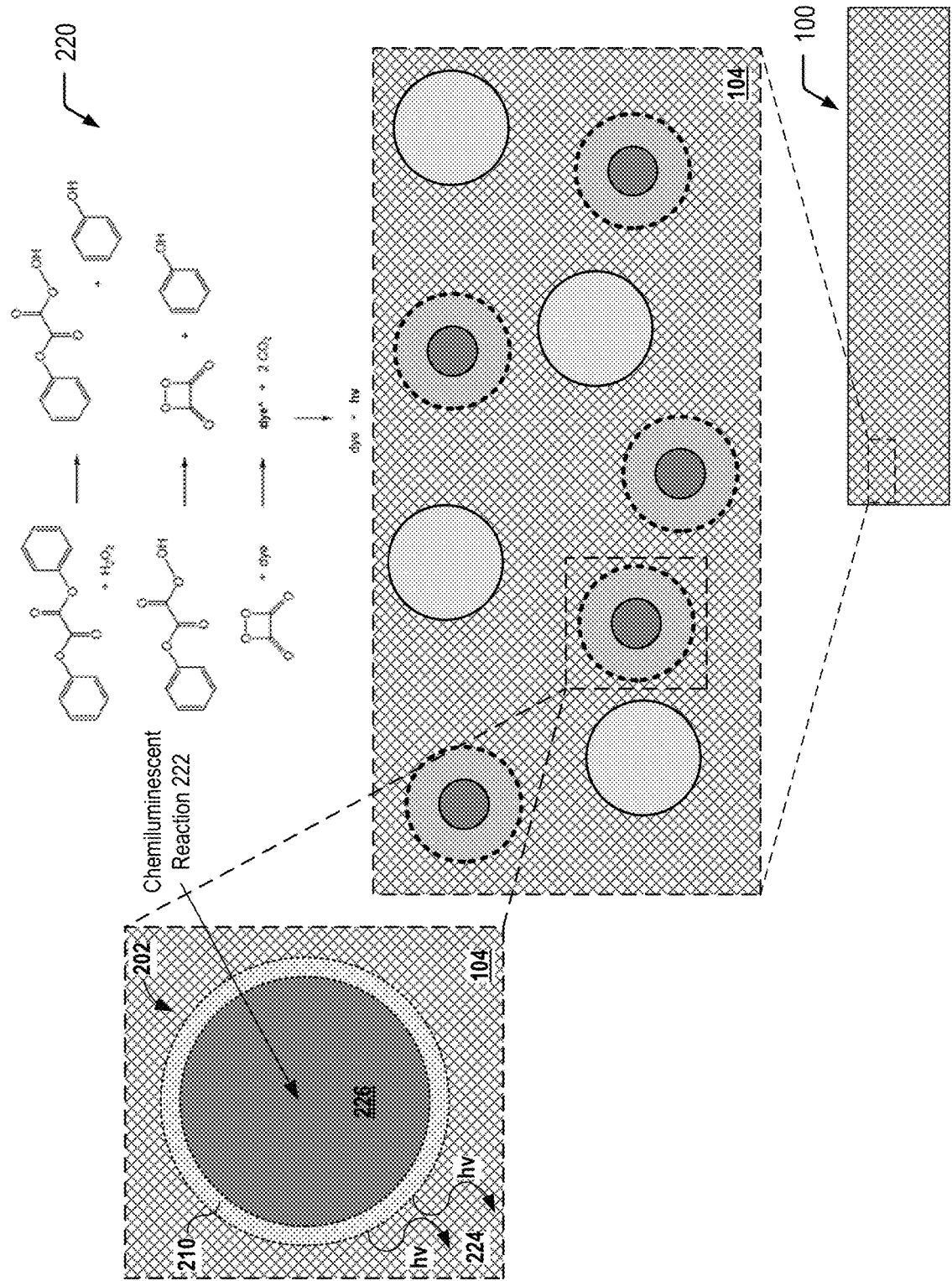
FIG. 2B is a cross-sectional view of the multiple-compartment microcapsule of FIG. 2A after a compressive force results in rupture of an inner compartment of the microcapsule to enable the reactants to undergo the chemiluminescent reaction within the microcapsule, according to one embodiment.

FIG. 2B illustrates an exploded cross-sectional view 220 of the individual multiple-compartment microcapsule 202 depicted in FIG. 2A after application of a compressive force to the multiple-compartment microcapsule 202. FIG. 2B illustrates that compression of the multiple-compartment microcapsule 202 depicted in FIG. 2A results in rupture of the capsule wall 216 of the inner microcapsule 212 to allow the first reactant(s) 214 and the second reactant(s) 218 to mix and undergo a chemiluminescent reaction 222. As described further herein with respect to FIG. 3C, a crack in the self-healing polymeric matrix material 104 may result in rupture of the capsule wall 216 of the inner microcapsule 212, allowing the reactants to mix and undergo the chemiluminescent reaction 222. FIG. 2B further illustrates that, in some embodiments, application of the compressive force does not result in rupture of the outer wall 210 of the multiple-compartment microcapsule 202.

FIG. 2B illustrates that the chemiluminescent reaction 222 that occurs within the microcapsule 202 generates light 224 (identified as "hv" in FIG. 2B), and the outer shell 210 of the microcapsule 202 allows a substantial portion of the light 224 (or particular wavelength(s) of the light 224) to pass through the outer shell 210 into the surrounding self-healing polymeric matrix material 104 (as well as into a crack that is formed in the self-healing polymeric matrix material 104 and filled with the monomer mixture, as shown in the example of FIG. 3C). As described further herein, the light 224 is within a particular wavelength range that is satisfactory to trigger a particular photoinitiator to initiate polymerization (e.g., free radical polymerization) of the monomers that have filled the crack (as shown in FIGS. 3A and 3B) in order to prevent further propagation of the crack (as shown in FIG. 3C).

FIG. 2B further illustrates that the multiple-compartment microcapsule 202 may contain a reaction product 226 of the reaction of the first reactant(s) 214 and the second reactant(s) 218 (as shown in FIG. 2A). As the outer wall 210 may remain intact after application of the compressive force, the outer wall 210 may prevent the reaction product 226 from contacting the self-healing polymeric matrix material 104.

The chemical reaction diagram depicted in FIG. 2B represents an illustrative, non-limiting example of a chemiluminescent reaction that may occur within the light generating microcapsule 202. The example chemiluminescent reaction depicted in FIG. 2B corresponds to a reaction of a suitable dye with diphenyl oxalate and a suitable oxidant such as hydrogen peroxide to produce a photon-emitting reaction. In a particular embodiment, the multiple-compartment microcapsule 202 may contain a mixture of a dye and diphenyl oxalate in the inner microcapsule 212 as the second reactant(s) 218 and may contain hydrogen peroxide as the first reactant(s) 214 surrounding the inner microcapsule 212. FIG. 2B illustrates that a product of a chemical reaction between diphenyl oxalate and hydrogen peroxide is 1,2-dioxetanedione that has an unstable strained ring, which decomposes spontaneously to carbon dioxide and releases energy that excites a dye, and the excited dye subsequently releases a photon as it returns to its ground state.

The top portion of the chemical reaction diagram illustrates a diphenyl oxalate molecule reacting with a hydrogen peroxide molecule to form two phenol molecules and one 1,2-dioxetanedione molecule. The middle portion of the chemical reaction diagram illustrates that the 1,2-dioxetanedione molecule, having an unstable strained ring, decomposes spontaneously to carbon dioxide and releases energy that excites a dye (with the excited die identified as "dye*" in FIG. 2B). The bottom portion of the chemical reaction diagram illustrates that the excited dye then releases a photon as it returns to its ground state, with "hv" representing the standard notation referring to release of radiant energy other than heat during the reaction.

The wavelength of the photon that is released as the excited dye returns to its ground state depends on the structure of a particular dye that is selected. To illustrate, different dyes may have different photon emission spectral distributions. Similarly, different photoinitiators may have different photoinitiator absorbance spectral distributions. A photon emission spectral distribution associated with a particular dye may be used to identify peak emission region(s), and the peak emission region(s) may be compared to a photoinitiator absorbance spectral distribution associated a particular photoinitiator to determine whether the particular photoinitiator is sufficiently absorbent in the peak emission region(s). As such, a particular combination of a dye and a photoinitiator may be selected such that a wavelength of a photon emitted when the excited dye returns to its original state is satisfactory to excite the photoinitiator to initiate polymerization of the monomers. In some cases, the emission peak(s) in a photon emission spectral distribution associated with a particular dye may be compared to a spectral distribution associated with a light source (e.g., a mercury arc lamp) that is typically utilized to photo-cure a polymer/adhesive. A photoinitiator (or multiple photoinitiators) may be identified as satisfactory for the individual emission peaks in the spectral distribution associated with the light source.

As an illustrative, non-limiting example, the dye may be 9,10-diphenylanthracene which has a marked emission peak at 405 nm and appreciable emission at 436 nm. In this case, an illustrative, non-limiting example of a photoinitiator with a satisfactory photoinitiator absorbance spectral distribution is Ciba® IRGACURE™ 784 from Ciba Specialty Chemicals Inc. It will be appreciated that numerous combinations of dyes and photoinitiators may be suitable to initiate polymerization of a particular set of monomers (e.g., acrylate monomers).

Thus, FIGS. 2A and 2B illustrate an example of a light generating microcapsule of the present disclosure before application of a compressive force (FIG. 2A) and after application of the compressive force (FIG. 2B). As described further herein, the chemiluminescent reaction within the light generating microcapsule may generate light that is within a particular wavelength range that is satisfactory to trigger a particular photoinitiator to initiate polymerization of a particular set of monomers that fill a crack in a self-healing polymeric matrix material.

FIG. 3A illustrates a cross-sectional view 300 of selected portions of the article of manufacture 100 of FIG. 1 at a first stage of propagation of a crack 302 in the self-healing polymeric matrix material 104. In FIG. 3A, a monomer mixture 304 (that includes the monomers and the photoinitiator, as previously described herein) is shown as being encapsulated within an individual monomer mixture microcapsule 306 of the plurality of monomer mixture microcapsules 106 depicted in FIG. 1. Thus, the first stage of propagation of the crack 302 depicted in FIG. 3A shows the encapsulation of the monomer mixture 304 prior to rupture of the individual monomer mixture microcapsule 306.

FIG. 3B illustrates a cross-sectional view 310 of selected portions of the article of manufacture 100 of FIG. 1 at a second stage of propagation of the crack 302, resulting in microcapsule rupture 312 of the individual monomer mixture microcapsule 306 depicted in FIG. 3A. FIG. 3B further illustrates that the microcapsule rupture 312 enables the monomer mixture 304 to fill the crack 302 in the self-healing polymeric matrix material 104. Thus, the second stage of propagation of the crack 302 depicted in FIG. 3B shows the monomer mixture 304 filling the crack 302 prior to rupture of the individual light generating microcapsule 202.

FIG. 3C illustrates a cross-sectional view 320 of selected portions of the article of manufacture 100 of FIG. 1 at a third stage of propagation of the crack 302, resulting in application of a compressive force 322 to the individual light generating microcapsule 202 of the plurality of light generating microcapsules 102 dispersed in the self-healing polymeric matrix material 104. The compressive force 322 triggers the chemiluminescent reaction (identified by the reference character 222 in FIG. 3C) within the light generating microcapsule 202, causing the photoinitiator in the monomer mixture 304 to initiate polymerization of the monomers of the monomer mixture 304 within the crack 302. FIG. 3C illustrates that polymerization of the monomer mixture 304 results in formation of a polymerized material 324 within the crack 302, thereby preventing further propagation of the crack 302.

Thus, FIGS. 3A-3C illustrate an example in which propagation of a crack that is formed in a self-healing polymeric matrix material (see FIG. 3A) causes a monomer mixture microcapsule to rupture and release an encapsulated monomer mixture into the crack (see FIG. 3B). FIG. 3C illustrates that further propagation of the crack results in application of a compressive force to a light generating microcapsule that triggers a chemiluminescent reaction within the light generating microcapsule. The emitted light has sufficient energy to excite a photoinitiator (in the monomer mixture that has filled the crack, as shown in FIG. 3B) to initiate polymerization (e.g., free radical polymerization) of the monomers in the crack. FIG. 3C further illustrates that polymerization of the monomers results in the formation of a polymerized material within the crack, thereby preventing further propagation of the crack.

Figure 4:
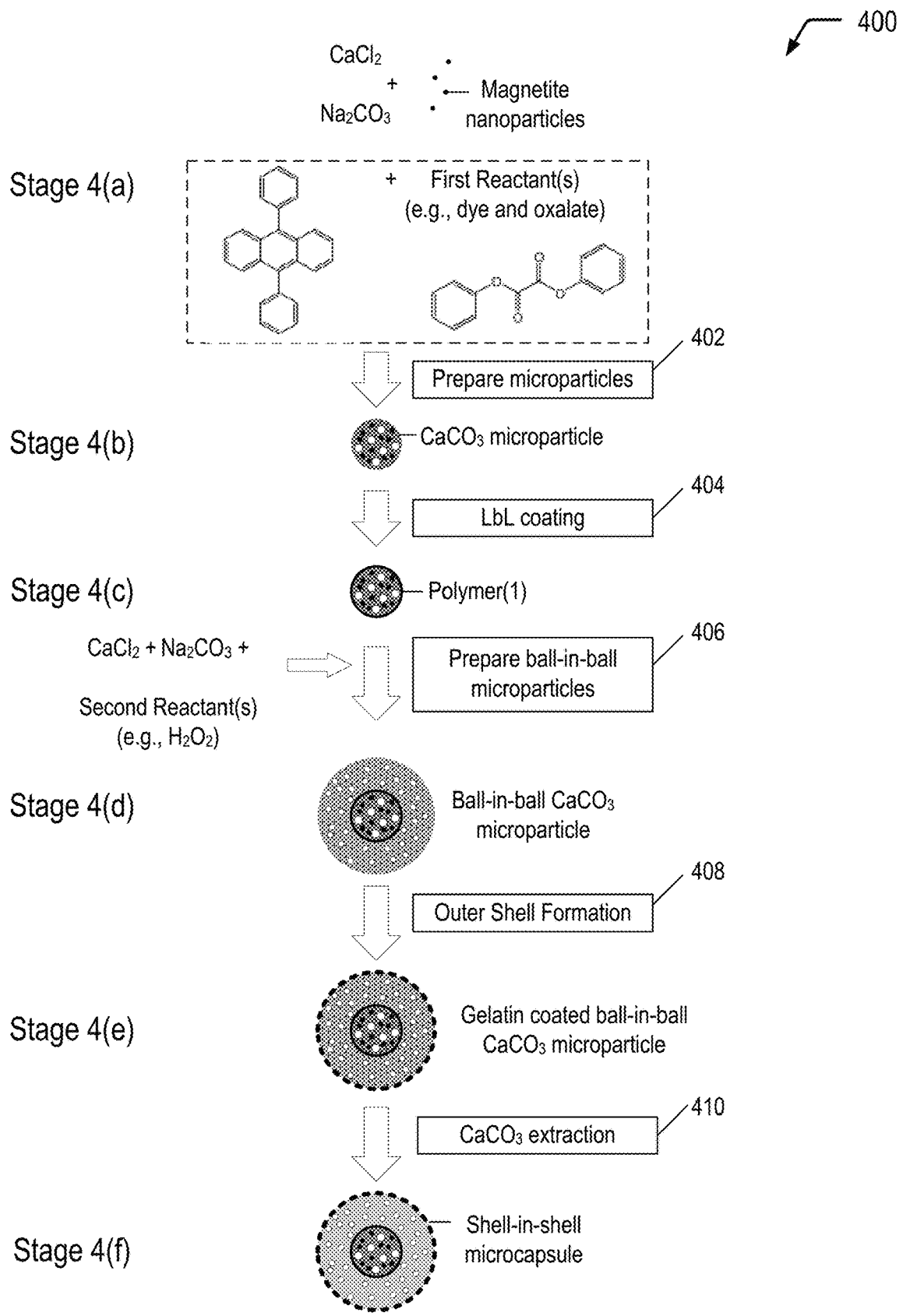
FIG. 4 is a flow diagram illustrating a method of producing a multiple-compartment microcapsule having a shell-in-shell architecture with an inner shell contained within an outer shell, where the inner shell is adapted to rupture in response to application of a compressive force to cause a chemiluminescent reaction within the microcapsule, according to some embodiments.

FIG. 4 is a flow diagram illustrating, through stages 4(a) to 4(f), an example of a method 400 of producing a multiple-compartment microcapsule having a shell-in-shell architecture with an inner shell contained within an outer shell, where the inner shell is adapted to rupture in response to application of a compressive force to cause a chemiluminescent reaction within the microcapsule, according to some embodiments. In each of the stages 4(a)-4(f), the structure is shown in a cross-sectional side view. The microcapsule produced in FIG. 4 may correspond to the multiple-compartment microcapsule 202 depicted in FIG. 2A that represents one of the light generating microcapsules 102 depicted in FIG. 1.

Referring to FIG. 4, and according to an embodiment, the shell-in-shell microcapsules can be made using any reactants and oxidants of any chemiluminescent reaction (identified as "First Reactant(s)" and "Second Reactant(s)" in FIG. 4). For example, First Reactant(s) may be a dye and diphenyl oxalate, and Second Reactant(s) may be an oxidant such as hydrogen peroxide. Once the inner shell ruptures, the reactants mix and emit photons. One skilled in the art will understand that a variety of chemiluminescent reactants can be used. Both the First Reactant(s) and the Second Reactant(s) may comprise one or more chemicals, particles, and combinations thereof.

In the example depicted in FIG. 4, magnetic nanoparticles are used in operation 402 for incorporation into the "inner core" $CaCO_3$ microparticles (shown at stage 4(b)). Magnetic nanoparticles are incorporated into the "inner core" $CaCO_3$ microparticles for the purpose of subsequently magnetically isolating the product prepared in operation 406 (i.e., ball-in-ball $CaCO_3$ microparticles) from a coproduct (i.e., single core $CaCO_3$ microparticles). The magnetic nanoparticles may be, for example, $Fe_3O_4$ (also referred to as "magnetite") nanoparticles, cobalt ferrite nanoparticles or other magnetic nanoparticles known in the art. In a particular embodiment, the magnetic nanoparticles may have a diameter in a range of approximately 6 nm to 25 nm.

An example of a technique of preparing magnetite nanoparticles follows. A 5 mol/l NaOH solution is added into a mixed solution of 0.25 mol/l ferrous chloride and 0.5 mol/l ferric chloride (molar ratio 1:2) until obtaining pH 11 at room temperature. The slurry is washed repeatedly with distilled water. Then, the resulting magnetite nanoparticles are magnetically separated from the supernatant and redispersed in aqueous solution at least three times, until obtaining pH 7. A typical average diameter of the resulting magnetite nanoparticles may be about 12 nm.

The microparticle system described with respect to FIG. 4 is based on $CaCO_3$ microparticles that are hardened by formation of a polyelectrolyte multilayer around the $CaCO_3$ microparticles. The method 400 begins by preparing spherical calcium carbonate microparticles in which magnetite nanoparticles and First Reactant(s) (e.g., diphenyl oxalate and a dye, such as 9,10-diphenylanthracene) are immobilized by coprecipitation (operation 402). For example, 1M $CaCl_2$ (0.615 mL), 1M $Na_2CO_3$ (0.615 mL), 1.4% (w/v) magnetite nanoparticle suspension (50 μL), First Reactant(s) (0.50 mg dye and 133 mg oxalate), and deionized water (2.450 mL) may be rapidly mixed and thoroughly agitated on a magnetic stirrer for about 20 seconds at about room temperature. After the agitation, the precipitate may be separated from the supernatant by centrifugation and washed three times with water. One of the resulting $CaCO_3$ microparticles is shown at stage 4(b).

The diameter of the $CaCO_3$ microparticles produced with a reaction time of 20 seconds is about 4 μm to about 6 μm. Smaller $CaCO_3$ microparticles are produced if the reaction time is reduced from about 20 seconds to about several seconds. One skilled in the art will appreciate that other magnetic nanoparticles may be used in lieu of, or in addition to, the magnetite. For example, cobalt ferrite nanoparticles may also be used.

In this example, the fabrication of polyelectrolyte capsules is based on the layer-by-layer (LbL) self-assembly of polyelectrolyte thin films. Such polyelectrolyte capsules are fabricated by the consecutive adsorption of alternating layer of positively and negatively charged polyelectrolytes onto sacrificial colloidal templates. Calcium carbonate is but one example of a sacrificial colloidal template. One skilled in the art will appreciate that other templates may be used in lieu of, or in addition to, calcium carbonate.

The method 400 continues by LbL coating the $CaCO_3$ microparticles (operation 404). In operation 404, a polyelectrolyte multilayer (PEM) build-up may be employed by adsorbing five bilayers of negative PSS (poly(sodium 4-styrenesulfonate); Mw=70 kDa) and positive PAH (poly(allylamine hydrochloride); Mw=70 kDa) (2 mg/mL in 0.5M NaCl) by using the layer-by-layer assembly protocol. For example, the $CaCO_3$ microparticles produced in operation 402 may be dispersed in a 0.5M NaCl solution with 2 mg/mL PSS (i.e., polyanion) and shaken continuously for 10 min. The excess polyanion may be removed by centrifugation and washing with deionized water. Then, 1 mL of 0.5M NaCl solution containing 2 mg/mL PAH (i.e., polycation) may be added and shaken continuously for 10 min. The excess polycation may be removed by centrifugation and washing with deionized water. This deposition process of oppositely charged polyelectrolyte may be repeated five times and, consequently, five PSS/PAH bilayers are deposited on the surface of the $CaCO_3$ microparticles. One of the resulting polymer coated $CaCO_3$ microparticles is shown at stage 4(c).

The thickness of this "inner shell" polyelectrolyte multilayer may be varied by changing the number of bilayers. Generally, it is desirable for the inner shell to rupture while the outer shell remains intact. Typically, for a given shell diameter, thinner shells rupture more readily than thicker shells. Hence, in accordance with some embodiments of the present disclosure, the inner shell is made relatively thin compared to the outer shell. On the other hand, the inner shell must not be so thin as to rupture prematurely.

The PSS/PAH-multilayer in operation 404 is but one example of a polyelectrolyte multilayer. One skilled in the art will appreciate that other polyelectrolyte multilayers and other coatings may be used in lieu of, or in addition to, the PSS/PAH-multilayer in operation 404.

The method 400 continues by preparing ball-in-ball calcium carbonate microparticles in which Second Reactant(s) (which can be any suitable oxidant, including hydrogen peroxide) is immobilized by a second coprecipitation (operation 406). "Immobilize" means "removing from general circulation, for example by enclosing in a capsule." The ball-in-ball $CaCO_3$ microparticles are characterized by a polyelectrolyte multilayer that is sandwiched between two calcium carbonate compartments. In operation 406, the polymer coated $CaCO_3$ microparticles may be resuspended in 1M $CaCl_2$ (0.615 mL), 1M $Na_2CO_3$ (0.615 mL), and deionized water (2.500 mL) containing hydrogen peroxide (1 mg), rapidly mixed and thoroughly agitated on a magnetic stirrer for about 20 seconds at about room temperature. After the agitation, the precipitate may be separated from the supernatant by centrifugation and washed three times with water. The second coprecipitation is accompanied by formation of a coproduct, i.e., single core $CaCO_3$ microparticles that contain only hydrogen peroxide. Hence, the resulting precipitate represents a mixture of ball-in-ball $CaCO_3$ microparticles and single core $CaCO_3$ microparticles. The ball-in-ball $CaCO_3$ microparticles, which are magnetic due to the immobilized magnetite nanoparticles in the inner compartment, may be isolated by applying an external magnetic field to the sample while all of the nonmagnetic single core $CaCO_3$ microparticles are removed by a few washing steps. One of the resulting ball-in-ball $CaCO_3$ microparticles is shown at stage 4(d).

The method 400 continues by coating the ball-in-ball $CaCO_3$ microparticles (operation 408). In an embodiment, the outer shell wall material is made of a material for the chemiluminescent photon to escape the shell. In another embodiment, the outer shell wall material is made of a material where the photon yield outside the wall of the outer shell wall is maximized. In an embodiment, the outer shell wall has a transmittance of at least 90%. In certain embodiments, the outer shell wall material may include natural polymeric material, such as gelatin, arabic gum, shellac, lac, starch, dextrin, wax, rosin, sodium alginate, zein, and the like; semi-synthetic polymer material, such as methyl cellulose, ethyl cellulose, carboxymethyl cellulose, hydroxyethyl ethyl cellulose; full-synthetic polymer material, such as polyolefins, polystyrenes, polyethers, polyureas, polyethylene glycol, polyamide, polyurethane, polyacrylate, epoxy resins, among others. In certain embodiments, the method for wrapping a core material includes chemical methods such as interfacial polymerization, in situ polymerization, molecular encapsulation, radiation encapsulation; physicochemical methods such as aqueous phase separation, oil phase separation, capsule-heart exchange, pressing, piercing, powder bed method; and physical methods, such as spray drying, spray freezing, air suspension, vacuum evaporation deposition, complex coacervation, long and short centrifugation.

An example of a conventional technique of preparing the outer shell follows, and can be accomplished at stage 4(e). A gelatin is dissolved into n-hexane in a water bath at about 50° C. to obtain a 6% gelatin solution. The gelatin may optionally be swelled with deionized water before the preparation of the gelatin solution. The ball-in-ball $CaCO_3$ microparticles prepared in operation 406 are added to the gelatin solution while stirring to form an emulsified dispersion system. The pH is then adjusted to about 3.5-3.8 using acetic acid, and then a 20% sodium sulfate solution is slowly added into the dispersion system while maintaining a temperature of about 50° C. The temperature of the dispersion system is then lowered to a temperature of about 15° C. The result is a colloid of gelatin coated ball-in-ball $CaCO_3$ microparticles.

Generally, it is desirable for the inner shell to rupture while the outer shell remains intact so that the reactants and the reaction products do not contaminate the material into which the multi-compartment microcapsule is dispersed. Typically, for a given shell diameter, thinner shells rupture more readily than thicker shells. Hence, in accordance with some embodiments of the present disclosure, the outer shell is made relatively thick compared to the inner shell.

Operation 410 is a $CaCO_3$ extraction. In operation 410, the $CaCO_3$ core of the ball-in-ball $CaCO_3$ microparticles may be removed by complexation with ethylenediaminetetraacetic acid (EDTA) (0.2M, pH 7.5) leading to formation of shell-in-shell microcapsules. For example, the gelatin coated ball-in-ball $CaCO_3$ microparticles produced in operation 408 may be dispersed in 10 mL of the EDTA solution (0.2M, pH 7.5) and shaken for about 4 h, followed by centrifugation and re-dispersion in fresh EDTA solution. This core-removing process may be repeated several times to completely remove the $CaCO_3$ core. The size of the resulting shell-in-shell microcapsules ranges from about 8 μm to about 10 μm, and the inner core diameter ranges from about 3 μm to about 5 μm. One of the resulting shell-in-shell microcapsules is shown at stage 4(f). Depending on the application of use, the shell-in-shell microcapsule can have a range of about 0.5 μm to about 200 μm.

As noted above, the fabrication of polyelectrolyte capsules in the method 400 of FIG. 4 is based on the layer-by-layer (LbL) self-assembly of polyelectrolyte thin films. One skilled in the art will appreciate that a multi-compartment microcapsule for light generation in accordance with some embodiments of the present disclosure may be produced by other conventional multi-compartment systems, such as polymeric micelles, hybrid polymer microspheres, and two-compartment vesicles.

As noted above, one skilled in the art will understand that various chemiluminescent reactants and oxidants can be used. Moreover, the multi-compartment microcapsule can utilize various chemiluminescent reactions. The chemistry used in chemiluminescent reactions is a mature technology, and those skilled in the art will know that additional materials can be further added to the multi-compartment microcapsule. For example, enhancing reagents such as alkyl dimethyl benzyl quaternary ammonium salt may be added to the reactants.

The photon-emitting reactants may be chosen to be inert with respect to the material of the microcapsule walls, or an isolating barrier within a microcapsule when the reactants are not in contact. The photon-emitting reactants also may be chosen to be inert with respect to the outer microcapsule wall when the reactants are in contact, or such that the chemical products of the reaction are inert with respect to the outer microcapsule wall, and any remnants of the inner microcapsule wall or barrier.

An amount of the first reactant(s) and an amount of the second reactant(s) may be determined. The amounts may be determined from the total amount of the reactants required to produce a desired amount of photons, the ratio of each reactant according to a reaction equation, the desired dimensions of the microcapsule, and the manner of isolating the reactants within the capsule. For example, a microcapsule may be desired having a maximum dimension less than or equal to a desired final thickness of less than 0.5 microns, and the amount of reactants may be chosen corresponding to the volume available within a microcapsule formed according to that dimension.

Thus, FIG. 4 illustrates an example of a process of forming a multiple-compartment microcapsule having an inner shell adapted to rupture when exposed to a compressive force in order to trigger a chemiluminescent reaction within the microcapsule. The multiple-compartment microcapsule formed according to the process depicted in FIG. 4 may correspond to the multiple-compartment microcapsule 202 illustrated and described further herein with respect to FIG. 2A.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A self-healing polymeric material comprising:
a polymeric matrix material;
wherein dispersed within the polymeric matrix material is a mixture of materials that includes monomers and a photoinitiator; and
a plurality of light generating microcapsules dispersed in the polymeric matrix material, each light generating microcapsule of the plurality of light generating microcapsules encapsulating multiple reactants that undergo a chemiluminescent reaction, wherein each light generating microcapsule comprises an outer shell and an inner shell,
wherein the chemiluminescent reaction generates a photon having a wavelength within a particular emission range that is consistent with an absorption range of the photoinitiator and wherein the chemiluminescent reaction occurs without rupture of the outer shell of the light generating microcapsules.

2. The self-healing polymeric material of claim 1, wherein a crack in the polymeric matrix material causes migration of the monomers and photoinitiator into the crack.

3. The self-healing polymeric material of claim 2, wherein further propagation of the crack in the polymeric matrix material results in application of a compressive force to a light generating microcapsule of the plurality of light generating microcapsules, the compressive force triggering the chemiluminescent reaction within the light generating microcapsule.

4. The self-healing polymeric material of claim 3, wherein the photon generated within the light generating microcapsule exits the light generating microcapsule into the crack to trigger the photoinitiator to initiate a polymerization reaction of the monomers within the crack, the polymerization reaction resulting in formation of a polymeric material that seals the crack.

5. The self-healing polymeric material of claim 4, wherein the photoinitiator includes a free radical initiator, and wherein the polymerization reaction includes a free radical polymerization reaction.

6. The self-healing polymeric material of claim 1, wherein the monomers include acrylate monomers.

7. The self-healing polymeric material of claim 1, wherein the chemiluminescent reaction includes excitation of a dye from a ground state to an excited state and subsequent release of the photon upon relaxation from the excited state to the ground state.

8. The self-healing polymeric material of claim 7, wherein excitation of the dye is caused by energy released during decomposition of a 1,2-dioxetanedione molecule.

9. The self-healing polymeric material of claim 8, wherein a chemical reaction of a diphenyl oxalate molecule with a hydrogen peroxide molecule results in formation of the 1,2-dioxetanedione molecule.

10. The self-healing polymeric material of claim 7, wherein the dye includes 9,10-diphenylanthracene.

11. The self-healing polymeric material of claim 1, wherein each light generating microcapsule includes a multiple-compartment microcapsule that comprises:
 a first compartment that contains a first reactant of the multiple reactants;
 a second compartment that contains a second reactant of the multiple reactants; and
 wherein the inner shell is an isolating structure separating the first compartment from the second compartment, the isolating structure adapted to rupture in response to application of a compressive force to cause the first reactant and the second reactant to undergo the chemiluminescent reaction.

12. The self-healing polymeric material of claim 11, wherein the multiple-compartment microcapsule includes a shell-in-shell microcapsule and the inner shell is contained within the outer shell, wherein the inner shell encapsulates the first compartment, wherein the outer shell encapsulates the second compartment.

13. The self-healing polymeric material of claim 12, wherein the outer shell comprises a polymer, and wherein the outer shell has a transmittance value of at least 90% for the wavelength within the particular emission range.

14. The self-healing polymeric material of claim 13, wherein the polymer comprises gelatin, arabic gum, shellac, lac, starch, dextrin, wax, rosin, sodium alginate, zein, methyl cellulose, ethyl cellulose, carboxymethyl cellulose, hydroxyethyl ethyl cellulose, polyolefins, polystyrenes, polyethers, polyesters, polyureas, polyethylene glycol, polyamides, polyimides, urea-formaldehydes, polyurethane, polyacrylate, epoxy resins, and combinations thereof.

15. The self-healing polymeric material of claim 1, wherein the outer shell remains intact during the chemiluminescent reaction, thereby preventing a reaction product of the chemiluminescent reaction from contacting the polymeric matrix material.

16. The self-healing polymeric material of claim 1, wherein the plurality of light generating microcapsules are adapted such that a compressive force caused by a crack in the polymeric matrix material ruptures the inner shell without rupturing the outer shell, thereby causing the multiple reactants to mix and initiate the chemiluminescent reaction within the plurality of light generating microcapsules.

17. A self-healing polymeric material comprising:
 a polymeric matrix material;
 a mixture of monomers and a photoinitiator dispersed within the polymeric matrix material; and
 a plurality of light generating microcapsules dispersed in the polymeric matrix material, each light generating microcapsule comprising an outer shell and an inner shell, wherein the inner shell is adapted to rupture in response to a compressive force that does not rupture the outer shell,
 wherein each light generating microcapsule encapsulates multiple reactants that undergo a chemiluminescent reaction within the respective light generating microcapsule in response to the inner shell rupturing,
 wherein the chemiluminescent reaction generates a photon having a wavelength within a particular emission range that is consistent with an absorption range of the photoinitiator, and
 wherein the chemiluminescent reaction occurs without rupture of the outer shell of the light generating microcapsules.

18. The self-healing polymeric material of claim 17, wherein the outer shell comprises a polymer, and wherein the outer shell has a transmittance value of at least 90% for the wavelength within the particular emission range.

19. The self-healing polymeric material of claim 17, wherein the outer shell comprises a plastic that is adapted to filter the light generated by the chemiluminescent reaction such that greater than 90% of photons having a wavelength within the particular emission range pass through the outer shell, while fewer photons having a wavelength outside the particular emission range are able to pass through the outer shell.

20. The self-healing polymeric material of claim 17, wherein the mixture of monomers and the photoinitiator are not encapsulated.

* * * * *